United States Patent [19]

Tovey

[11] Patent Number: 5,445,140
[45] Date of Patent: Aug. 29, 1995

[54] ENDOSCOPIC SURGICAL DEVICE

[75] Inventor: H. Jonathan Tovey, Milford, Conn.

[73] Assignee: United States Surgical Corporation, Norwalk, Conn.

[21] Appl. No.: 72,701

[22] Filed: Jun. 7, 1993

[51] Int. Cl.⁶ ............................................. A61B 1/008
[52] U.S. Cl. ................................. 600/117; 604/281; 606/78; 600/129
[58] Field of Search ................ 128/751, 17, 20, 4, 128/40 M; 606/78; 604/281, 95

[56] References Cited

U.S. PATENT DOCUMENTS

| | | |
|---|---|---|
| 3,314,431 | 4/1967 | Smith, Jr. . |
| 3,620,212 | 11/1971 | Fannon et al. . |
| 3,890,977 | 6/1975 | Wilson .................... 604/281 |
| 4,665,906 | 5/1987 | Jervis . |
| 4,688,555 | 8/1987 | Wardle . |
| 4,763,669 | 8/1988 | Jaeger . |
| 4,773,431 | 9/1988 | Lodomirski .............. 604/264 X |
| 4,880,015 | 11/1989 | Nierman . |
| 4,944,741 | 7/1990 | Hasson . |
| 4,945,920 | 8/1990 | Clossick . |
| 5,037,178 | 8/1991 | Stoy et al. . |
| 5,106,369 | 4/1992 | Christmas ................ 128/20 X |
| 5,122,155 | 6/1992 | Eberbach . |
| 5,152,279 | 10/1992 | Wilk . |
| 5,254,130 | 10/1993 | Poncet et al. ............ 606/206 |
| 5,281,236 | 1/1994 | Bagnato et al. .......... 604/281 X |
| 5,290,310 | 3/1994 | Makower et al. ........ 128/DIG. 8 X |

FOREIGN PATENT DOCUMENTS 990220 1/1983 U.S.S.R. .

OTHER PUBLICATIONS

"Development of Polymeric Shape Memory Material", Sirai et al., Dec. 1988.
"Shape Memory Polymer", Mitsubishi Heavy Industries America, 1992.
"Processing Instructions For Mitsubishi Shape Memory Polymer", Manual No. 1, Rev. 2.2, Mitsubishi Heavy Industries, Ltd., Apr. 1992.
"Tinel® Shape-Memory Metal", Raychem Corporation, Jul. 1984.
"Shape Memory Metal", Raychem Corporation, May 1989.
"Designing With The Shape Memory Effect", Duerig et al., MRS Int'l. Mtg. on Adv. Mats., vol. 9, 1989.

*Primary Examiner*—Richard J. Apley
*Assistant Examiner*—Beverly A. Meindl

[57] ABSTRACT

The invention described herein provides a surgical apparatus for use in endoscopic or laparoscopic procedures having a hand manipulatable proximal end portion, a working distal end portion, and a and a hinge member disposed between the end portions. The hinge member provides articulation of the distal end and is made from a temperature-responsive material which is substantially rigid at ambient temperatures and which is tractable above a predetermined temperature.

15 Claims, 1 Drawing Sheet

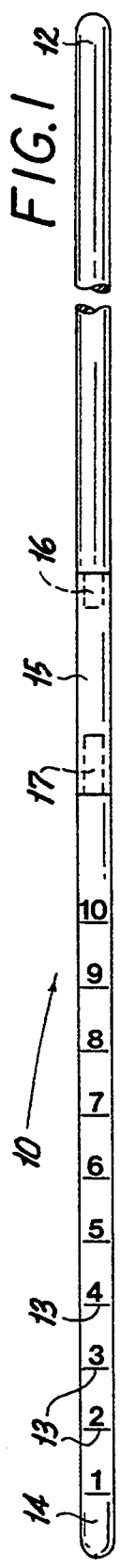
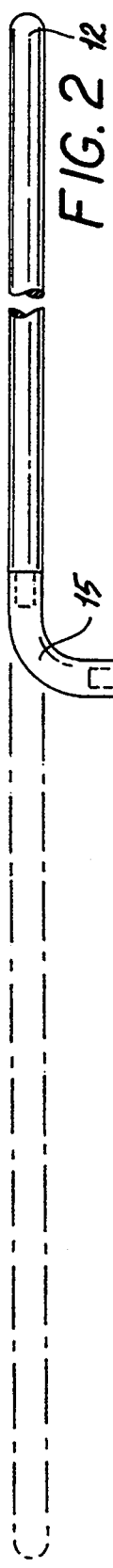
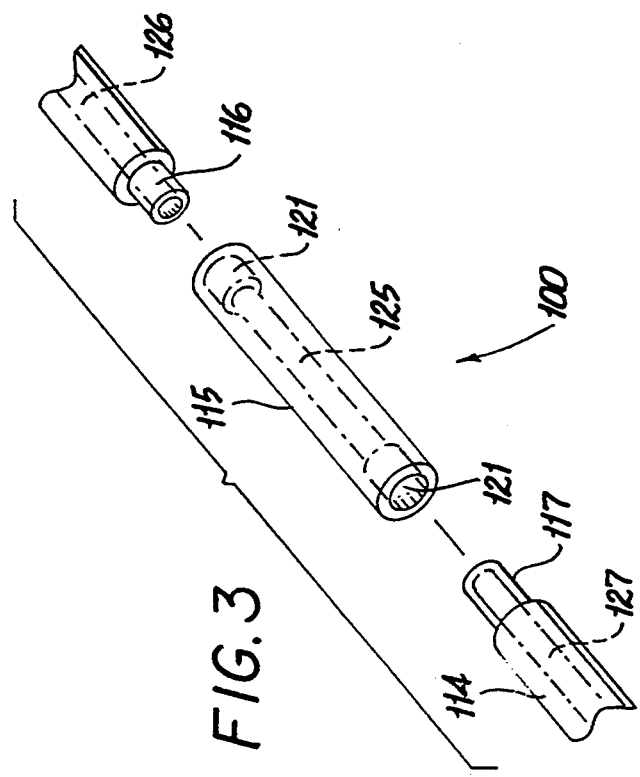

ENDOSCOPIC SURGICAL DEVICE

BACKGROUND OF THE INVENTION

1. Field of the Invention

This invention relates to surgical apparatus, and more particularly, to apparatus having an articulating working end for use during endoscopic or laparoscopic surgical procedures.

2. Description of Related Art

In laparoscopic and endoscopic procedures, surgery is performed through a small incision made in the patient's body, generally to provide access for a trocar or cannula device. Once extended into the patient's body, the cannula device permits insertion of a variety of surgical instruments including scissors, graspers, a clip applier and staplers.

Surgical instruments having an articulating working end for use in endoscopic and laparoscopic surgical procedures are also known in the art. In the past, articulation of the working end of the instrument has been provided through the use of mechanical linkages having a plurality of moving parts. However, instruments having linkage assemblies are often relatively expensive to manufacture.

It is therefore an object of the subject invention to provide a surgical instrument having an articulating working end, preferably for use in endoscopic and laparoscopic procedures, which is inexpensive to manufacture.

It is another object of the subject invention to provide a surgical instrument having an articulating working end for use in endoscopic or laparoscopic procedures which has a minimum number of external moving parts.

These and other objects of the surgical apparatus of the subject invention will become more readily apparent from the following detailed description of the invention.

SUMMARY OF THE INVENTION

A novel surgical apparatus is provided for performing surgical tasks, particularly during endoscopic or laparoscopic procedures. The apparatus comprises a handle portion adapted to remain at least in part outside the body during surgery, a working end adapted to be inserted into the body during surgery, and a hinge member located between the handle end and the working end. The hinge member is manufactured from a material which changes shape and elasticity at about body temperature. In a particularly useful embodiment of the subject invention, the hinge member of the instrument is formed of a thermoplastic material having a glass transition temperature in the range of about 20° C. to 40° C. Preferably, the hinge member is formed of polyurethane having a glass transition temperature of about 25° C.

In another embodiment of the subject invention, the hinge member includes a passageway formed therethrough. The passageway is preferably adapted to receive means for causing actuation of the working end of the instrument in response to manipulation of the handle end of the instrument. In particularly useful embodiments the actuation means is bendable at least in the portion actually positioned within the passageway in the hinge member.

The provision of hinge members configured to provide various degrees of articulation is within the scope of the present invention. For example, the shape of the hinge member may deform to define substantially a fight angle when placed within the body, or may easily be deformed to that attitude by pressure against tissue as the hinge member is easily deformable at body temperature.

Further features of the subject invention will become more readily apparent from the following detailed description of the invention taken in conjunction with the drawings.

BRIEF DESCRIPTION OF THE DRAWINGS

Preferred embodiments of the subject invention are described hereinbelow with respect to the drawings wherein:

FIG. 1 is a perspective view of a surgical apparatus in accordance with a preferred embodiment of the subject invention prior to insertion into a body;

FIG. 2 is a perspective view of the surgical apparatus of FIG. 1 after insertion into a body with the hinge member thereof in an articulated position; and FIG. 3 is a partial exploded perspective view of another embodiment of the apparatus of the invention prior to insertion into a body.

DETAILED DESCRIPTION OF THE PREFERRED EMBODIMENTS

Because endoscopic procedures are more common than laparoscopic procedures, the present invention shall be discussed in terms of endoscopic procedures and apparatus. However, use herein of terms such as "endoscopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to laparoscopic procedures.

In the drawings and in the description which follows, the term "proximal", as is traditional, will refer to the end of the apparatus which is closest to the operator, while the term "distal" will refer to the end which is furthest from the operator.

Referring now in detail to the drawings, wherein like reference numerals identify similar elements, a surgical apparatus for performing tasks during endoscopic or laparoscopic procedures in accordance with a preferred embodiment of the subject invention is illustrated in FIG. 1 and is designated generally by reference numeral 10. Surgical apparatus 10 comprises a handle portion 12 and a working end portion 14. Portions 12 and 14 may be formed of a firm, lightweight, plastic material such as, for example, LEXAN brand material which is marketed by General Electric Corporation. A hinge member 15 is located between portions 12 and 14.

The term handle portion is intended to broadly embrace a portion of the instrument which remains at least in part outside the patient's body during surgery, and which is hand manipulatable. The handle portion may include switches, triggers, valves, connectors, gauges, dials, etc. which may serve, for example, as adjustment or actuation means for the device or as an indicator. The handle portion may also include a grip to facilitate comfortable holding or manipulation of the device.

In the embodiment shown in the Figures, the working end portion 14 of the instrument is provided with graduations 13 and thus can function as a measuring device. It should be understood that the configuration or type of working end portion provided on the apparatus of this invention may be any of the known types of surgical tools. Thus, for example, the working end may be adapted to serve as a retractor, cutting device, manipulator, applicator, clip applier, electrocautery device, laser device, swab, suturing device, optical device, etc.

Hinge member 15 is mounted at the distal end of portion 12 by any conventional means. For example, a shank 16 of reduced diameter may be provided at the distal end of portion 12, to be received and secured within a recess (not shown) formed within hinge member 15. Hinge member 15 may be similarly attached to the proximal end of portion 14 via shank 17. Other methods for securing the hinge member to portions 12 and 14 (such as, for example providing threads on shanks 16, 17 and corresponding threads within receiving bores in hinge member 15) will be apparent to those skilled in the art. The cross-sectional diameters of portions 12, 14 and hinge member 15 are preferably substantially equal and are suitably dimensioned for endoscopic utilization.

Hinge member 15 is formed from a material which changes shape and elasticity when the temperature of the material is raised to about body temperature. Hinge member 15 is preferably formed of a thermoplastic material having a glass transition temperature in the range of about 20° C. to 40° C. It is within this temperature range that the internal body temperatures of most warm blooded animals lie. The specific glass transition temperature of the material from which hinge member 15 is formed however, will depend upon the subject being operated on. For example, in veterinary procedures, the preferred glass transition temperature of the material will differ from that which is preferred in surgical procedures involving human subjects. Preferably, for surgical procedures involving human subjects the material from which hinge member 15 is formed is polyurethane having a glass transition temperature of about 25° C. Therefore, at temperatures above about 25° C. (i.e. inside the patient's body), the polyurethane material from which hinge member 15 is formed will exhibit easily deformable attributes. Conversely, at temperatures below about 25° C. (i.e. outside the patient's body), hinge member 15 will remain substantially rigid. Suitable polyurethanes include those manufactured by Mitsubishi Heavy Industries America and distributed by Memry Technologies, Inc., Brookfield, Conn. under the tradenames MM, MS Solution and MP. The benefits of this thermoplastic material will become more readily apparent from the discussion which follows.

In use, the apparatus may be introduced into the abdominal cavity of a patient through an incision or, alternatively, through a trocar or cannula device (not shown) which is inserted into a small incision in the patient's body. Because hinge member 15 remains substantially firm at room temperature, its insertion through the trocar or cannula device is smooth; it does not buckle since its modulus of elasticity is high. However, once extended into the abdomen, the thermotropic material from which hinge member 15 is formed, advantageously becomes tractable. As explained hereinabove, the change in rigidity of hinge member 15 is due to the relationship between the glass transition temperature of the material and the body temperature of the patient. In particularly useful materials, the stiffness of the hinge will continue to decrease as the temperature of the hinge increases above the glass transition temperature of the material from which the hinge member is formed. Accordingly, once introduced to the operative site, the patient's body temperature, which is preferably above the glass transition temperature of the material, causes hinge member 15 to become flexible and conform to its preformed shape. In this flexible state, the angular orientation between the working end of the instrument and the handle portion can be changed by pressing the working end against internal body structures. For example, in the instrument shown in FIGS. 1 and 2, the graduated measuring portion can be deflected by pressing against internal body structure to lie parallel to the feature to be measured.

Preferably, as illustrated in FIG. 2, the preformed shape of hinge member 15 is a substantially right angle configuration such that, when fully deployed, the working end portion 14 of the instrument is generally perpendicular to the handle portion 12 of the instrument. Other hinge configurations are envisioned, including, for example, hinges defining angles other than 90°. It is envisioned that a variety of hinge members each of which attains a different angular orientation may be provided in a kit with a surgical instrument, thereby affording the operator maximum flexibility in his choice of the degree of articulation exhibited by the instrument.

Turning now to FIG. 3, another surgical apparatus in accordance with a preferred embodiment of the subject invention is illustrated and is designated generally by reference numeral 100. Surgical apparatus 100 generally comprises a tubular body having an elongated passageway. The passageway is formed by passageway 126 extending through at least a portion of handle portion 112, passageway 127 extending through at least a portion of working end 114 and passageway 125 extending through hinge member 115. Preferably, the diameters of passageways 125, 126 and 127 are the same so as to form a smooth, continuous passageway when portions 112, 114 and hinge member 115 are joined together.

As in the previously discussed embodiment, hinge member 115 may be attached to the distal end of portion 112 via a shank of reduced diameter 116. Shank 116 is received and secured within recess 121 formed in hinge member 115. Similarly, hinge member 115 may be attached to the proximal end portion 114 via shank 117. Other methods of securing portions 112, 114 and 115 together will be apparent to those skilled in the art.

The operation and materials of construction for the embodiment shown in FIG. 3 are generally the same as in the previously discussed embodiment, with the hinge member 115 being made from a material which exhibits substantial rigidity at ambient conditions and becomes tractable at body temperature.

The passageways 125, 126 and 127 are dimensioned to receive actuating means for causing actuation of the working end portion 114 of the instrument in response to manipulation of the handle portion 112 of the instrument. Exemplary actuation means which may be received by the passageways include, but are not limited to rods, cables and pushers. The actuating means may be operably connected, for example, to a trigger on the handle portion 112 in such a way that operation of the trigger remotely opens or closes a jaw or scissor mechanism at the working end 114 of the instrument. The design of such actuation structures are within the skill of those in the art.

As another example, wires or fiber optic cables may extend through the passageway whereby activation of a switch on the handle portion 112 of the instrument causes the flow of electrical or laser energy to the working end portion 114 of the instrument to achieve cautery, cutting or welding of tissue.

Preferably, the actuation means received within passageway 125 are flexible in the area of hinge member 115 so as to not interfere with the articulation of the device.

Although the surgical apparatus of the subject invention has been described with respect to a preferred embodiment, it is apparent that changes or modifications made be made thereto without departing from the spirit or scope of the invention as defined by the appended claims. To the extent not already indicated, it will also be understood by those of ordinary skill in the art that any of the various embodiments herein described and illustrated may be further modified to incorporate features shown in another of the embodiments.

What is claimed is:

1. In an endoscopic instrument having a proximal, handle portion and an articulating distal, working end portion, the improvement comprising an articulation-providing hinge member made from a temperature responsive thermoplastic resin which is substantially rigid at ambient temperatures and which is tractable above a predetermined temperature, wherein at least a portion of the elongated working distal end portion is rigid.

2. An instrument as in claim 1 wherein said material is a thermoplastic resin having a glass transition temperature between about 20° and 40° C.

3. An instrument as in claim 2 wherein said material is a polyurethane.

4. An instrument as in claim 1 wherein said hinge member is deformable above said pre-determined temperature to provide an angle of less than 180° but not less than 90° between the proximal handle portion and the working end portion.

5. An instrument as in claim 4 wherein said angle is about 90°.

6. In an endoscopic instrument having a proximal, handle portion and an articulating distal, working end portion, the improvement comprising an articulation-providing hinge member made from a temperature responsive thermoplastic resin which is substantially rigid at ambient temperatures and which is tractable above a predetermined temperature, the hinge member having an axial passageway adapted for receiving actuation means for causing actuation of said distal working end of said instrument in response to manipulation of the handle portion of said instrument.

7. An endoscopic surgical instrument comprising:
    a proximal handle portion;
    an elongated working distal end portion, at least a portion of the elongated working distal end portion being rigid;
    said proximal and distal end portions being moveable between a first position wherein said portions are axially aligned and a second position wherein the longitudinal axes of said portions are oriented at an angle less than 180° but not less than 90°; and
    a hinge member located between said end portions and made from a temperature-responsive thermoplastic resin which is substantially rigid at ambient temperatures and which is tractable above a predetermined temperature.

8. An instrument as in claim 7 wherein said material is a thermoplastic resin having a glass transition temperature between about 20° C. and 40° C.

9. An instrument as in claim 8 wherein said material is a polyurethane.

10. An instrument as in claim 7 wherein said hinge member is deformable above said predetermined temperature to provide an angle of less than 180° but not less than 90° between the proximal handle portion and the working end portion.

11. An instrument as in claim 7 wherein said angle is about 90°.

12. An instrument as in claim 7 wherein working end includes graduations.

13. An endoscopic surgical instrument comprising:
    a proximal handle portion;
    an elongated working distal end portion;
    said proximal and distal end portions being moveable between a first position wherein said portions are axially aligned and a second position wherein the longitudinal axes of said portions are oriented at an angle less than 180° but not less than 90°; and
    a hinge member located between said end portions and made from a temperature-responsive thermoplastic resin which is substantially rigid at ambient temperatures and which is tractable above a predetermined temperature, the hinge member having an axial passageway adapted for receiving actuation means for causing actuation of said distal working end of said instrument in response to manipulation of the handle portion of said instrument.

14. An endoscopic surgical method comprising:
    a) inserting a working end of a surgical instrument through a cannula, said instrument including a handle portion, a hinge and a working end, said hinge being fabricated from a material which is rigid at ambient temperature and tractable at body temperature;
    b) allowing said hinge to increase in temperature from ambient temperature to body temperature whereby said hinge becomes tractable;
    c) pressing said working end against an internal body structure such that the warmed hinge deforms and said working end is positioned at an angle relative to said handle portion.

15. A method as in claim 14 wherein said working end includes graduations.

* * * * *